United States Patent
Seong et al.

(10) Patent No.: US 10,342,807 B2
(45) Date of Patent: Jul. 9, 2019

(54) PHARMACEUTICAL COMPOSITION FOR PREVENTION, TREATMENT OR DELAY OF ALZHEIMER'S DISEASE OR DEMENTIA CONTAINING G PROTEIN-COUPLED RECEPTOR 19 AGENT AS ACTIVE INGREDIENT

(71) Applicant: SEOUL NATIONAL UNIVERSITY R&DB FOUNDATION, Seoul (KR)

(72) Inventors: Seung Yong Seong, Seoul (KR); Jung Ah Cho, Seoul (KR); Tae Joo Kim, Seoul (KR); Youn Hee Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 16/123,703

(22) Filed: Sep. 6, 2018

(65) Prior Publication Data

US 2019/0000863 A1    Jan. 3, 2019

Related U.S. Application Data

(63) Continuation of application No. 15/516,317, filed as application No. PCT/KR2016/000447 on Jan. 15, 2016, now Pat. No. 10,071,107.

(30) Foreign Application Priority Data

Jul. 6, 2015 (KR) .................. 10-2015-0095951

(51) Int. Cl.
*C07J 31/00* (2006.01)
*A61K 31/575* (2006.01)
(Continued)

(52) U.S. Cl.
CPC .............. *A61K 31/575* (2013.01); *A61K 9/00* (2013.01); *A61K 9/14* (2013.01); *A61K 9/20* (2013.01);
(Continued)

(58) Field of Classification Search
None
See application file for complete search history.

(56) References Cited

U.S. PATENT DOCUMENTS

| 2008/0031968 A1 | 2/2008 | Bianco et al. |
| 2008/0312332 A1 | 12/2008 | Pei et al. |
| 2015/0290219 A1 | 10/2015 | Seong et al. |

FOREIGN PATENT DOCUMENTS

| JP | 2004-346059 | 12/2004 |
| JP | 2010-523627 | 7/2010 |

(Continued)

OTHER PUBLICATIONS

"Cerebral amyloid angiopathy", downloaded from the internet at https://en.wikipedia.org/wiki/Cerebral_amyloid_angiopathy (Year: 2018).*

(Continued)

*Primary Examiner* — Karl J Puttlitz
(74) *Attorney, Agent, or Firm* — Rubin and Rudman, LLP

(57) ABSTRACT

The present invention relates to a pharmaceutical composition for preventing, treating or delaying an Alzheimer's disease (AD) or dementia including a G protein-coupled receptor19 (GPCR19) agonist or its pharmaceutically acceptable salt as an active ingredient and a food composition for preventing, treating or delaying an Alzheimer's disease or dementia. The GPCR19 agonist according to the present invention has an effect of improving cognitive and behavioral disorders without harming the health of objects when administered to the objects and has an effect of (Continued)

preventing the Alzheimer's disease or dementia or delaying or treating the progression of the disease in the objects with the disease by suppressing apoptosis of the brain tissue, enhancing immunity, and reducing formation of an amyloid β (Aβ) plague.

6 Claims, 10 Drawing Sheets

(51) Int. Cl.
 *A61K 9/00* (2006.01)
 *A61K 9/14* (2006.01)
 *A61K 9/20* (2006.01)
 *A61P 25/28* (2006.01)
 *A61K 31/10* (2006.01)
 *A61K 31/16* (2006.01)

(52) U.S. Cl.
 CPC .............. *A61K 31/10* (2013.01); *A61K 31/16* (2013.01); *A61P 25/28* (2018.01); *C07J 31/006* (2013.01); *Y02A 50/406* (2018.01)

(56) References Cited

FOREIGN PATENT DOCUMENTS

| KR | 10-2013-0103468 A | 9/2013 |
| KR | 10-2015-0029043 A | 3/2015 |
| WO | WO 2004/083867 A2 | 9/2004 |
| WO | WO 2015/030328 A1 | 3/2015 |

OTHER PUBLICATIONS

Thathiah, A. et al., "The Role of G Protein-Coupled Receptors in the Pathology of Alzheimer's Disease", Nature Reviews Neuroscience, 12:73-87 (2011).
English Translation of International Search Report of PCT/KR2016/000447 dated Jul. 28, 2016, WIPO, Korea.
English Translation of Japanese Office Action of JP 2017-505858 dated Dec. 21, 2017, Japanese Patent Office, Japan.
Database Caplus Chemical Abstracts Service, Columbus, Ohio, US; Database Accession No. 2016:695886, Abstract of Huang et al., Science Translation Medicine (2016, 7(309), 309ra164/1-309ra164/11 CODEN: STMCBQ; ISSN: 1946-6242 (Year:2015).

\* cited by examiner

PHARMACEUTICAL COMPOSITION FOR PREVENTION, TREATMENT OR DELAY OF ALZHEIMER'S DISEASE OR DEMENTIA CONTAINING G PROTEIN-COUPLED RECEPTOR 19 AGENT AS ACTIVE INGREDIENT

FIELD OF THE INVENTION

The present invention relates to a pharmaceutical composition for preventing, treating or delaying an Alzheimer's disease (AD) or dementia including a G protein-coupled receptor19 (GPCR19) agonist or its pharmaceutically acceptable salt as an active ingredient and a food composition for preventing, treating or delaying an Alzheimer's disease or dementia.

DESCRIPTION OF RELATED ART

An Alzheimer's disease (AD) is a chronic neurodegenerative disease which occupies 50 to 70% of dementia which causes cognitive loss due to gradual neuronal degeneration and is characterized by accumulation of 39 to 43 amino acid peptides called a β-amyloid protein (Aβ) in a fibrillary form which is present as an amyloid plaque and an amyloid in the brain tissue.

In the Alzheimer's disease, Aβ deposition is harmful to neurons and epileptic cells in the brain and as a result, causes brain inflammation and neuronal cell death which are characteristics of the Alzheimer's disease. Many different theories for pathogenesis of the AD have been published and one of the well-established theories proposes association of a cholinergic pathway and it is an ultimate generation process of the AD to cause a gradual reduction of acetylcholine as a neurotransmitter. The AD has pathological features deposition of Aβ generally related to oxidative stress state such as exposure to peroxynitrite (ONOO—) and superoxide ions ($O_2$—) and of τ-related neurofibrillary tangles.

The Alzheimer's disease is divided into a familial AD represented by a genetic factor and a sporadic AD occurring in a large number of patients although the exact cause is not known. The human AD patients exhibit complex cognitive deficits by exhibiting psychological signs such as failure of memory, increased anxiety, and mental and physical abnormalities including hypersensitivity reaction.

In the brains of patients deceased due to the AD, senile plaques and neurofibrillary tangles are represented as pathological features. The senile plaques are formed by accumulating proteins and dead cells, and the like at the outside of the cells and their main ingredient is a peptide called an amyloid-β (Aβ).

A gradual loss of a cognitive action, the major characteristic of AD patients, is caused by the abnormally accumulated Aβ. The Aβ is generated from an amyloid precursor protein (hereinafter, referred to as "APP") by a proteolysis process. The APP as the precursor is decomposed by β-secretase (BSCE) and γ-secretase to generate Aβ.

AD treating agents currently being used in various countries are mostly ACh protease inhibitor and include tacrine, aricept, and the like. In addition, pharmaceutical companies including Merck, Bayer, and the like are providing similar drugs to the market. In case of tacrine, side effects of hepatotoxicity are increased and treatment thereof is often stopped, and aricept which is recently developed has less side effects.

In order to promote synthesis of the ACh, several clinical trials in which choline, lecithin acetyl carnitine, and the like as precursors are administrated have been attempted, but these materials not pass through the blood-brain barrier and has an effect of a short period and thus do not receive attention in the present due to the shortcomings.

Meanwhile, ABT-418 as a nicotine receptor inhibitor, xanomeline as a muscarinic receptor inhibitor, lecithin and acetyl-L-carnitine as acetylcholine precursors, desfferioxamine and rioquinol as metal chelators, iAβ5 and iAβ11 as beta-sheet breakers, vitamin E, *ginkgo biloba* extract, melatonin, and idebenone of antioxidants, nicotine, acetylcholine, carbachol, and beta-secretase of sAPP release agents, OM99-1, OM99-2, OM99-3, and Z-VLL-CHO of gamma secretase inhibitors, NSAIDs-based drugs as anti-inflammatory agents, and the like have been developed. However, the effects are still slight enough to alleviate some pathologic symptoms or delaying the progression, or most of the materials are difficult to be actually applied due to their own toxicity and thus, development of stable and effective AD treating agents is urgent.

The inventors of the present invention found that the composition including sodium taurodeoxycholate as a GPCR19 agonist and its derivatives had an effect on Alzheimer's disease or dementia and propose the composition as a pharmaceutical ingredient for preventing, treating, improving, and delaying the Alzheimer's disease or dementia. Until now, examples of attempting to apply the composition including the sodium taurodeoxycholate and the derivatives thereof to improvement and treatment of the Alzheimer's disease or dementia are not yet known, and therapeutic effects of the Alzheimer's disease or dementia have not been reported.

PRIOR ARTS

Patent Literatures

KR patent No, 1,452,864 (2014 Oct. 14.)
KR patent No. 1,494,275 (2015 Feb. 11.)
KR patent publication No. 2015-0029043 (2015 Mar. 18.)
KR patent No. 785,656 (2007 Dec. 7.)

Non-patent Literatures

Hardy, J. et al, Nat Neurosci. 1:355-358, 1998
Craven, R., Nat Rev. Neurosci. 2: 533, 2001; David, H. S. et al., Nat Rev. Neurosci. 2: 595-598, 2001
Yankner, B. A., Neuron 16: 921-932, 1996; Selkoe, D. J., Nature 399: A23-A31, 1999

SUMMARY OF INVENTION

Technical Problem

An objective of the present invention is to provide a composition for preventing, treating or delaying Alzheimer's disease or dementia including a GPCR19 agonist as an active ingredient, and more particularly, a composition for preventing, treating or delaying Alzheimer's disease or dementia including sodium taurodeoxycholate as one of GPCR19 agonists and derivatives thereof as an active ingredient. Much more particularly, the objective of the present invention is to provide an agent for preventing, treating or delaying Alzheimer's disease or dementia including sodium taurodeoxycholate and derivatives thereof as an active ingredient.

Solution to Problem

An aspect of the present invention provides a pharmaceutical composition for preventing, treating or delaying Alzheimer's disease or dementia including a GPCR19 agonist as an active ingredient or particularly, a pharmaceutical composition for preventing, treating or delaying an Alzheimer's disease or dementia including sodium taurodeoxycholate and derivatives thereof as an active ingredient, in which the pharmaceutical composition may be formulated in a form of injections or oral preparations and pharmaceutically acceptable additives may be additionally included therein.

Advantage Effects of Invention

A G protein-coupled receptor19 (GPCR19) agonist according to the present invention has an effect of improving cognitive and behavioral disorders without harming the health of objects when administered to the objects and has an effect of preventing the Alzheimer's disease or dementia or delaying or treating the progression of the disease in the objects with the disease by suppressing apoptosis of the brain tissue, enhancing immunity, and reducing formation of an amyloid β (Aβ) plague.

DETAILED DESCRIPTION OF THE INVENTION

Figure 1:
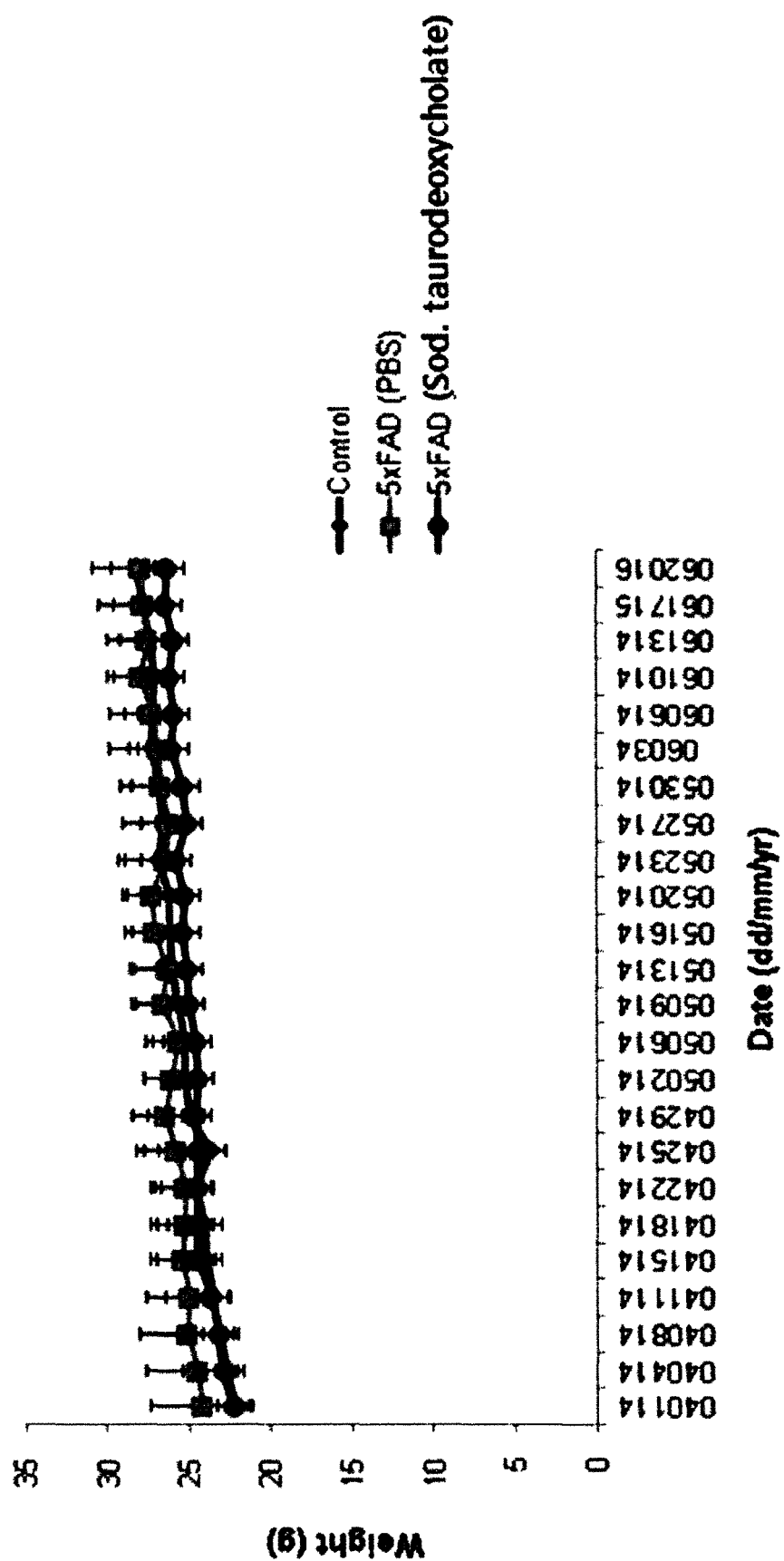
FIG. 1 illustrates a result of measuring a change in weight of a mouse after 1 mg/kg of PBS or sodium taurodeoxycholate is injected to a control mouse and an Alzheimer's mouse twice per week and a total of 20 times.

The present invention relates to a pharmaceutical composition for preventing, treating or delaying Alzheimer's disease (AD) or dementia including a G protein-coupled Receptor19 (GPCR19) agonist or pharmaceutically acceptable salts thereof as an active ingredient.

In an aspect of the present invention, the GPCR19 agonist is sodium taurodeoxycholate.

In an aspect of the present invention, the pharmaceutical composition may be formulated in forms of oral, rectal, intravenous, intramuscular, intraperitoneal, subcutaneous, intranasal formulations.

More particularly, the pharmaceutical composition may have any formulation selected from the group consisting of a tablet, a pill, a powder, a granule, a capsule, a suspension, a solution, an emulsion, a syrup, a sterilized aqueous solution, a nonaqueous solution, a suspension, an emulsion, a freeze-desiccant, a suppository, and an injection.

An administration path of the composition may be any general path as long as reaching a target tissue. The composition of the present invention may be orally, rectally, intravenously, intramuscularly, intraperitoneally, subcutaneously, and intranasally administrated, but is not limited thereto. Further, the composition may be administrated by any device in which the active material may be moved to the target cell.

In an aspect of the present invention, the pharmaceutical agent for oral administration may be present as a dose unit form such as a sugarcoated pill, a tablet, a pill, a powder, a granule, or a capsule and an ample. These agents are manufactured by a known method, for example, a general mixing, granulating, sugar-making, dissolving or freeze-drying method. For example, the pharmaceutical agent for oral administration may be prepared by mixing an active ingredient with a solid carrier, granulating the mixture, adding an appropriate additive if necessary, and then formulating the mixture or the granule in a form of a tablet or a sugarcoated pill.

The appropriate carrier may include, particularly, a filler, for example, sugar such as lactose, saccharose, mannitol or sorbitol, a cellulose agent, and/or calcium phosphate such as tricalcium phosphate or calcium hydrogen phosphate, and a coupling agent, for example, starch pastes using corn, wheat, rice or potato starches, gelatin, tragacanth, methylcellulose and/or polyvinylpyrrolidone, and if necessary, a disintegrating agent, for example, the aforementioned starches, carboxymethyl starch, crosslinked polyvinylpyrrolidone, agar or alginic acid or a salt thereof, for example, sodium alginate.

The additives include, particularly, a flow-control agent and a lubricant, for example, silicic acid, talc, stearic acid or its salt, for example, magnesium stearate or calcium, and/or polyethylene glycol. A gastric resistant appropriate coating is provided to a sugarcoated pill core, and particularly, a concentrated sugar solution including arabic gum, talc, polyvinyl pyrrolidone, polyethylene glycol and/or titanium dioxide in an appropriate organic solvent or a solvent mixture, or a rocker solution is used, or in order to form the gastric resistant coating, an appropriate cellulose agent solution such as acetylcellulose phthalate or hydroxypropylmethylcellulose phthalate may be used.

Other orally administered pharmaceutical agents include capsule agents, and dry-filled capsules made of gelatin, and soft sealed capsules made of gelatin and a plasticizer such as glycerol or sorbitol. The dry-filled capsule may include an active ingredient in a particulate form, for example, a filler such as lactose, a coupling agent such as starches, and/or a modifier such as talc or magnesium stearate, and a mixture with a stabilizer if appropriate. In the soft capsule, the active ingredient is dissolved or suspended in an appropriate liquid, for example, fatty oil, paraffin oil, or liquid polyethylene glycol and a stabilizer may be added herein.

A formulation for parenteral administration includes a sterile aqueous solution, a non-aqueous solution, a suspension, an emulsion, a lyophilizing agent, a suppository. The formulation for parenteral administration may be effective injections by various methods, for example, intravenous, intraarterial, intramuscular, intraperitoneal, intranasal, intradermal, and subcutaneous methods, preferably, the intravenous method. The liquid is preferably, an isotonic aqueous solution or a suspension which may be prepared from a lyophilizing agent including the active ingredient alone or in a combination of a pharmaceutically acceptable carrier before using. The pharmaceutical agent may be sterilized and/or may include additives such as preservatives, stabilizers, wetting agents and/or emulsifiers, solubilizers, salts for controlling osmotic pressure and/or buffers.

In particular, as the non-aqueous solution and the suspension, propylene glycol, polyethylene glycol, vegetable oils such as olive oil, injectable ester such as ethyl oleate, and the like may be used. As a matter of the suppository, witepsol, macrogol, tween 61, cacao butter, laurin, glycerol gelatin, and the like may be used.

In an aspect of the present invention, the GPCR19 agonist or its pharmaceutically acceptable salt may prevent, treat, or delay a disease selected from the group consisting of cerebral amyloid angiopathy, cognitive impairment-related disorders, mild cognitive impairment, Alzheimer's disease-related attention deficit symptoms, Alzheimer's disease-related neural degeneration, degenerative dementia, elderly dementia, senile dementia, cerebral vascular dementia, alcoholic dementia, parkinson's disease-related dementia, tic disorder, and an amyloid β-related disease as corticobasal ganglionic degeneration.

In an aspect of the present invention, the GPCR19 agonist or its pharmaceutically acceptable salt may prevent or treat an Alzheimer's disease or dementia by administrating a dose of 0.1 mg/kg/day to 1,000 mg/kg/day, specifically a dose of 1 mg/kg/day to 500 mg/kg/day, more specifically a dose of 10 mg/kg/day to 100 mg/kg/day to a warm-blooded animal of 75 kg.

In an aspect of the present invention, the GPCR19 agonist or its pharmaceutically acceptable salt may be administrated with an administration interval of 1 to 3 times per week, particularly, 1 to 2 times per week.

The dose and the administration interval of the GPCR19 agonist for using in the present invention may vary various factors, for example, individual conditions, such as availability and duration of the active ingredient, an administration method, gender, age, and weight of warm-blooded animals, and other severity of diseases and the like. The specific administration path and the dose may be selected by a doctor/vet in charge according to features of an object to be administrated, that is, conditions such as an age, a weight, a disease state, and a physical condition.

The present invention may be a formulation in a form in which at least one drug selected from the group consisting of a cognitive enhancer, a memory enhancer and a cholinesterase inhibitor is mixed with the GPCR19 agonist or its pharmaceutically acceptable salt.

More particularly, the GPCR19 agonist according to the present invention may be administered in a combination/mix with other drugs for preventing, treating or delaying the Alzheimer's disease or dementia. Accordingly, the present invention further includes a treating method of Alzheimer's disease or dementia patients including a combination treatment of the GPCR19 agonist and a different Alzheimer's disease or dementia preventing/treating agent.

The present invention relates to a food composition for preventing, treating or delaying Alzheimer's disease (AD) or dementia including a G protein-coupled Receptor19 (GPCR19) agonist or its pharmaceutically acceptable salt.

In an aspect of the present invention, the GPCR19 agonist is sodium taurodeoxycholate.

In an aspect of the present invention, the GPCR19 agonist or its pharmaceutically acceptable salt may be used for preventing, treating or delaying a disease selected from the group consisting of cerebral amyloid angiopathy, cognitive impairment-related disorders, mild cognitive impairment, Alzheimer's disease-related attention deficit symptoms, Alzheimer's disease-related neural degeneration, degenerative dementia, elderly dementia, senile dementia, cerebral vascular dementia, alcoholic dementia, parkinson's disease-related dementia, tic disorder, and an amyloid β-related disease as corticobasal ganglionic degeneration.

In the present invention, "including as the active ingredient" means including in a capacity range having an effect of preventing, treating or delaying Alzheimer's disease or dementia, and the capacity range may be changed according to severity and a formulation, and the number of application times may be changed according to an age, a weight, and a constitution of an object.

In the present invention, "treatment" includes partial recovery, improvement, and relief of the Alzheimer's disease or dementia as well as complete recovery of the Alzheimer's disease or dementia symptoms as a result obtained by applying the pharmaceutical composition of the present invention to an object with the Alzheimer's disease or dementia.

In the present invention, "prevention" means preventing the Alzheimer's disease or dementia symptoms from being generated in advance by suppressing or blocking symptoms including cognitive disorders, behavioral disorders, cranial nervous breakdown, and the like by applying the pharmaceutical composition of the present invention to the object with the Alzheimer's disease or dementia.

Further, in the present invention, "improvement" means including reducing, preventing, or treating the symptoms.

Further, in the present invention, "active ingredient" means an ingredient having the activity alone or having the activity together with a carrier without self-activity.

The pharmaceutical composition of the present invention is administrated by a pharmaceutically effective dose, and in the present invention, the term "pharmaceutically effective dose" means an amount which is sufficient to treat the diseases at a reasonable benefit/risk ratio applicable to medical treatment or improvement, and an effective dose level may be determined according to elements including a kind of disease of the patient, the severity, age, and sex of the patient, activity of a drug, sensitivity to a drug, a time of administration, a route of administration, and an emission rate, duration of treatment, and simultaneously used drugs and other elements well-known in the medical field.

In the present invention, the term "object" means all animals including the human in which the Alzheimer's disease or dementia is already caused or to be caused, and the composition including the GPCR19 agonist or sodium taurodeoxycholate or its derivative according to the present invention is administered to the object to efficiently prevent and improve the disease.

Further, the present invention provides a method for preventing, treating or delaying Alzheimer's disease (AD) or dementia including administrating a G protein-coupled Receptor19 (GPCR19) agonist or its pharmaceutically acceptable salt to an object with the Alzheimer's disease (AD) or dementia.

The object means all animals including the human in which the Alzheimer's disease or dementia is already caused or to be caused, and preferably includes human, horse, sheep, pig, goat, camel, dog, and the like, but the present invention is not limited thereto.

The administration means introducing a predetermined material to an object including the human by an appropriate method, and the GPCR19 agonist or its pharmaceutically acceptable salt according to the present invention may be orally administered through any general path capable of reaching a target tissue or parenterally administered (for example, intravenous, subcutaneous, intraperitoneal or topical application), and the active ingredient may be administrated by any device capable of moving to a target cell, and preferably administrated by a subcutaneous injection method.

The treatment includes partial recovery, improvement, and relief of the Alzheimer's disease or dementia symptoms as well as complete recovery of the Alzheimer's disease or dementia as a result obtained by applying the GPCR19 agonist or its pharmaceutically acceptable salt of the present invention to an object with the Alzheimer's disease or dementia.

The prevention means preventing the Alzheimer's disease or dementia symptoms from being caused in advance by suppressing or blocking symptoms including cognitive disorders, behavioral disorders, cranial nervous breakdown, and the like by applying the GPCR19 agonist or its pharmaceutically acceptable salt of the present invention to the object with the Alzheimer's disease or dementia or a health object.

The improvement means reduction, prevention, or treatment of the symptoms.

Further, the present invention provides a use of a G protein-coupled receptor19 (GPCR19) agonist or its pharmaceutically acceptable salt to be used as a pharmaceutical composition for preventing, treating or delaying Alzheimer's disease (AD) or dementia.

Further, the present invention provides a use of a G protein-coupled receptor19 (GPCR19) agonist or its pharmaceutically acceptable salt to be used as a food composition for preventing, treating or delaying Alzheimer's disease or dementia.

The GPCR19 agonist or its pharmaceutically acceptable salt according to the present invention has an effect of improving cognitive and behavioral disorders without harming the health of objects when administrated to the objects and may be used as the pharmaceutical composition or the food composition for preventing the Alzheimer's disease or dementia or delaying or treating the progression of the disease in the objects with the disease by suppressing apoptosis of the brain tissue, enhancing immunity, and reducing formation of an amyloid β (Aβ) plague.

Hereinafter, the present invention will be described in more detail through Examples and the like. However, Examples according to the present invention may be modified in various different forms and the scope of the present invention is not limited to the following Examples.

EXAMPLES

Experimental Example 1

Analysis of Weight Change and Behavioral Difference by Sodium Taurodeoxycholate in Alzheimer's Mouse Model (5×FAD)

[Experimental Method] 1 mg/kg of PBS or sodium taurodeoxycholate was injected to a control mouse (without an Alzheimer's gene) and an Alzheimer's mouse (4 per group) twice a week and a total of 20 times to measure the weight changes of the mice. The experimental result is illustrated in FIG. 1. As the experimental result, a rapid weight change of the mouse by drug administration in a sodium taurodeoxycholate administration group was not exhibited. It can be seen that the sodium taurodeoxycholate administration does not harm the health of the animal.

[Experimental Method: Morris Water maze] An acryl-made platform having a diameter of 10 cm was installed in a circular water tank having a size of diameter×height=150 cm×80 cm and a camera was installed at the center of the water tank on the ceiling where the water tank was placed. Around the water tank, a horizontal cue, a vertical grid cue, and a circular object cue were disposed, respectively. For the experimental preparation, water at about 26° C. was filled in the water tank up to a height of about 1 cm from the top of the platform and a white water paint was dissolved.

At a first experimental day, the mouse was flooded at one position of the prepared water tank and swam for 3 minutes and then induced to move to the platform location by an experimenter's hand after 3 minutes and left for 1 minute on the platform. After 1 minute, the mouse was lifted and covered by both hands and put in a cage again after 1 minute. This process was repeated three times. From the second experimental day, the mouse was flooded at one position ("first position") of the prepared water tank and a time until the mouse found the platform was recorded. Even after 90 seconds, when the mouse did not find the platform, the experimenter induced the mouse to move the platform location by a hand and when the mouse was placed on the platform, the mouse was left for 30 seconds and then the mouse was lifted and covered by both hands and then left for 1 minute. After 1 minute, the process was repeated at two different positions ("the second position" and "the third position") of the water tank and finally, the process was repeated at the "first position" again. The process was repeated everyday until a difference between mouse groups was decreased. At the final experimental day, the mouse was flooded in the water tank after removing the platform in the water tank and a video for 90 seconds was recorded and then a moving path and the number of platform pass times of the mouse in the water tank, a time latency of the platform location, and the like were analyzed by using analysis software.

Figure 2:
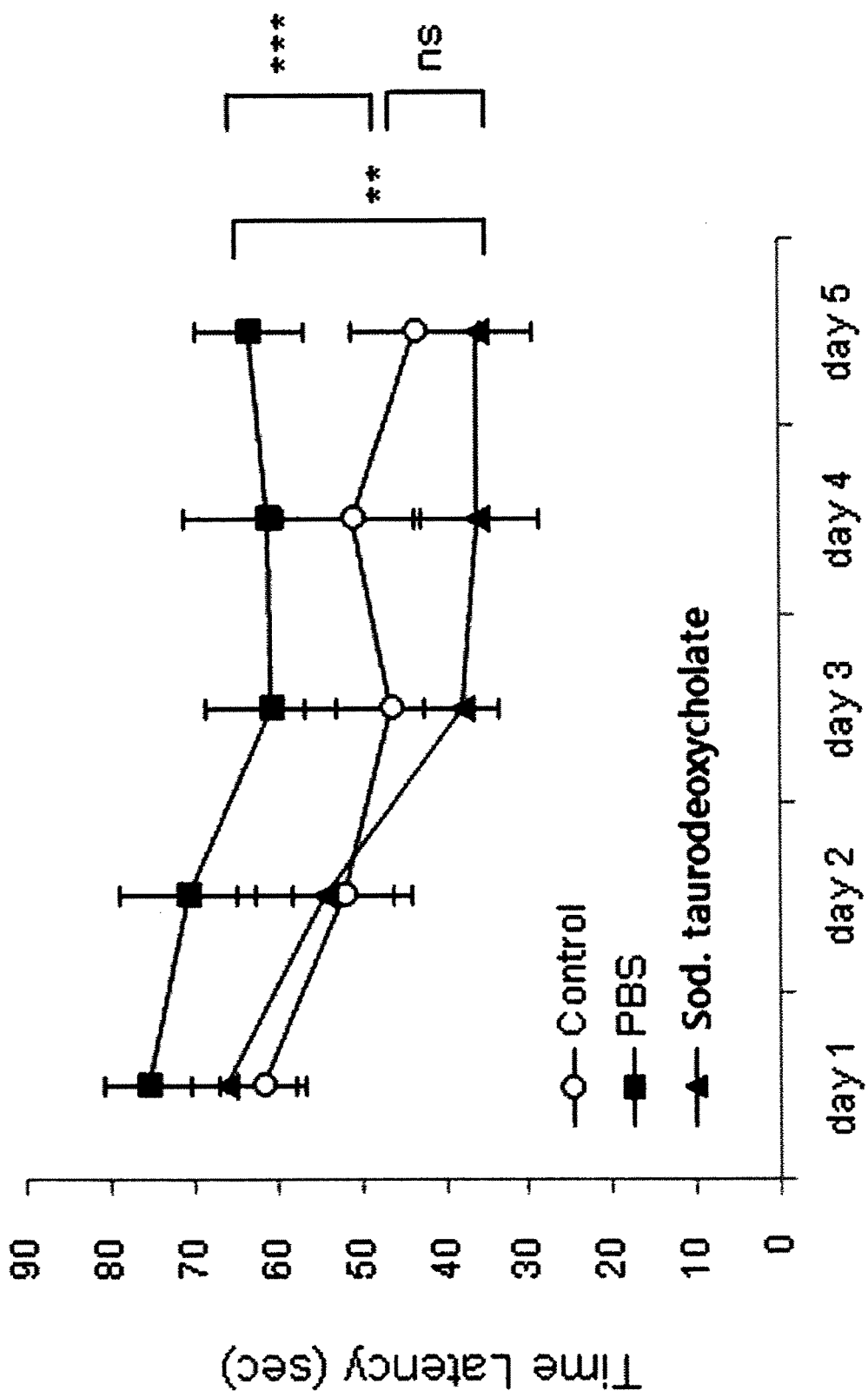
FIG. 2 illustrates a result of evaluating a spatial learning ability by performing an underwater labyrinth experiment after 1 mg/kg of PBS or sodium taurodeoxycholate is injected to a control mouse and an Alzheimer's mouse twice per week and a total of 20 times.

After 1 mg/kg of PBS or sodium taurodeoxycholate was injected to a control mouse and an Alzheimer's mouse (4 per group) twice a week and a total of 20 times, a result of evaluation a spatial learning ability through a water maze experiment was illustrated in FIG. 2. It was verified that a time required when the Alzheimer's mouse found the platform was shortened by administrating the sodium taurodeoxycholate drug.

Figure 3:
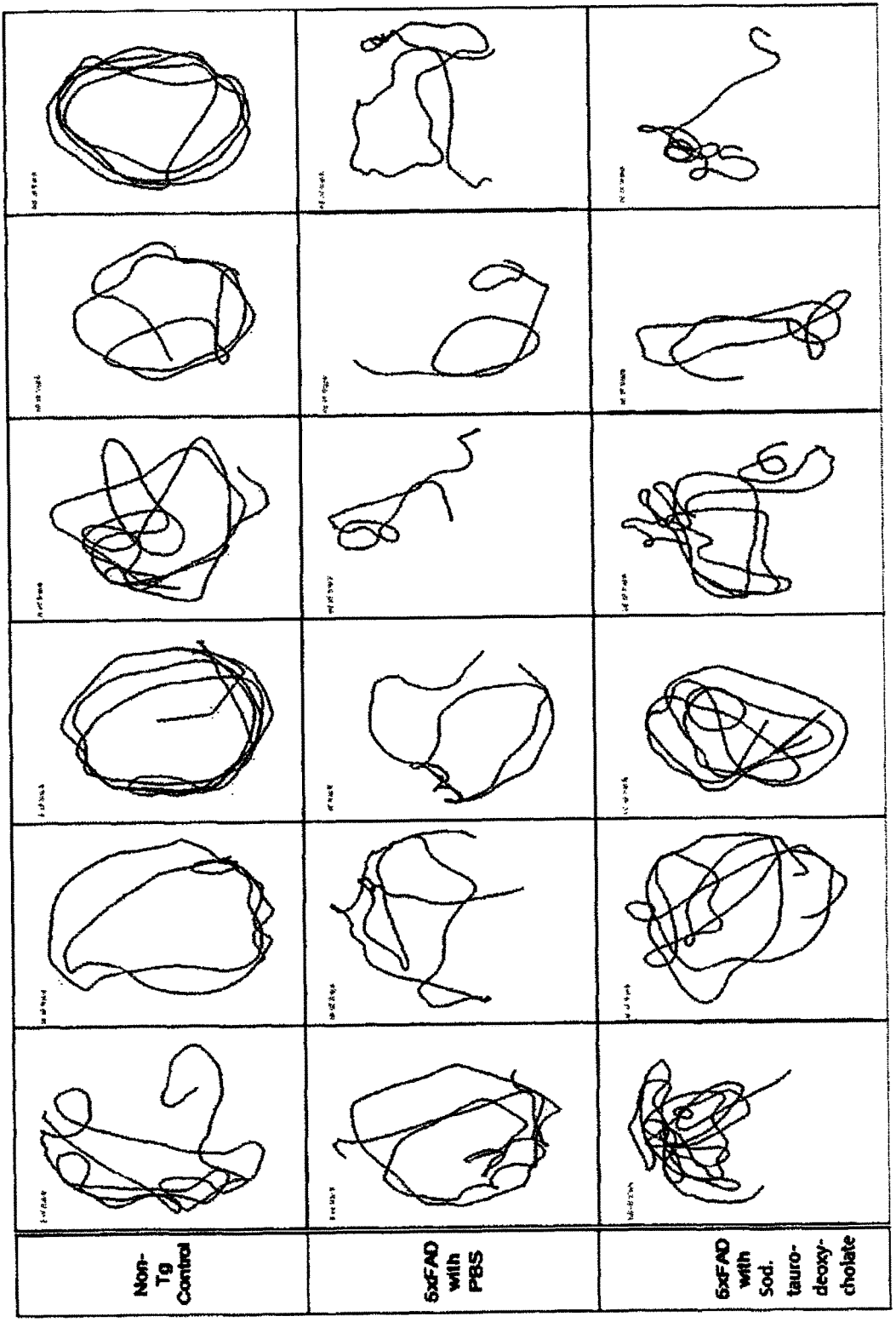
FIG. 3 illustrates a representative image of tracking a mouse behavior pattern in a water tank without a platform after 1 mg/kg of PBS or sodium taurodeoxycholate is injected to a control mouse and an Alzheimer's mouse twice per week and a total of 20 times.

After 1 mg/kg of PBS or sodium taurodeoxycholate was injected to a control mouse and an Alzheimer's mouse (more than 10 per group) twice a week and a total of 20 times, a mouse behavior pattern was tracked in the water tank without the platform. A representative image of the result of tracking the mouse movement in the water tank without the platform was illustrated in FIG. 3. In the sodium taurodeoxycholate administration mouse group, the moving pattern to the position of the platform was more actively observed.

Figure 4:
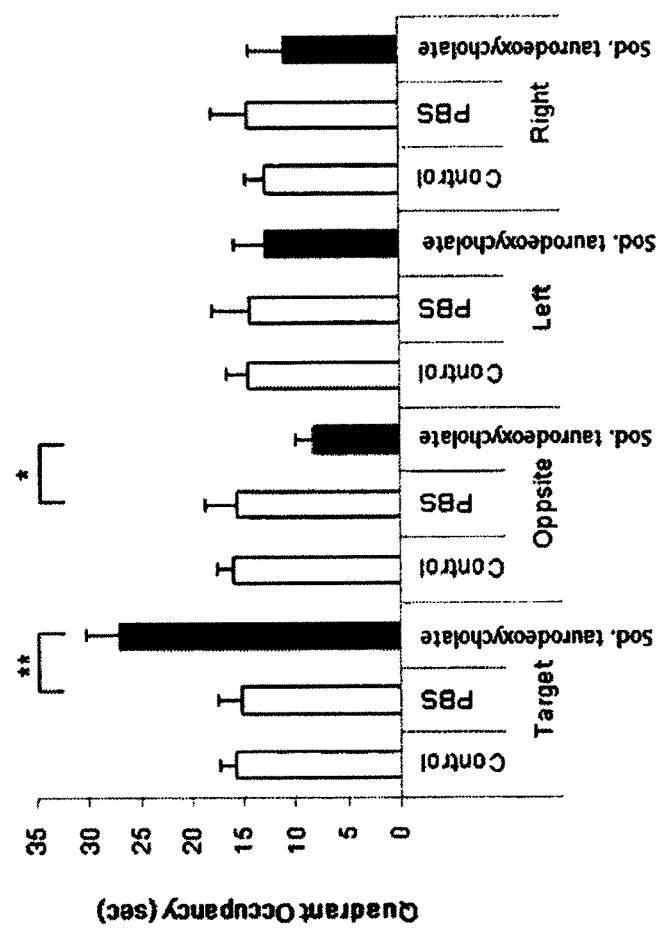
FIG. 4 illustrates a result of measuring the number of times of crossing the platform location and a time staying at the platform location in the mouse behavior pattern in the water tank without a platform after 1 mg/kg of PBS or sodium taurodeoxycholate is injected to a control mouse and an Alzheimer's mouse twice per week and a total of 20 times.
Figure 4:
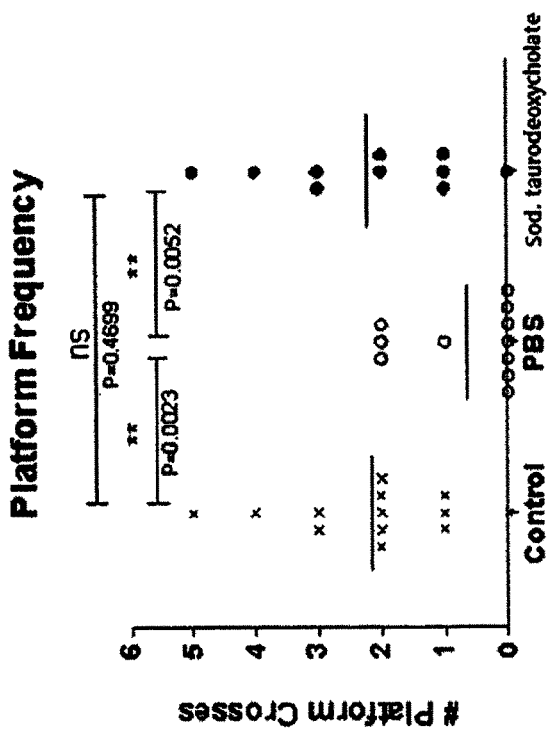

In the above experiment, the result of measuring the number of times when the mouse crossed the platform location and a time latency at the platform location was illustrated in FIG. 4 and in the sodium taurodeoxycholate administration mouse group, it was verified that the degree of memorizing the platform was high. In a probe test, as a result of comparing the number of times when the mouse for each experimental group crossed the platform location and the time latency, during the sodium taurodeoxycholate administration, the number of times of crossing the platform location and the time latency were significantly increased.

Experimental Example 2

Analysis of Change in Brain Tissue by Sodium Taurodeoxycholate in Alzheimer's Animal Model (5×FAD)

[Experimental Method: Tissue fluorescent staining] A mouse was anesthetized, the limbs were fixed and then the mouse was cut to expose the heart by scissors and tweezers. The upper right atrium was slightly cut by the scissors and punctured, a needle was put in the left ventricle, and PBS was injected and perfused. When the colors of the blood vessel and the organs turned to white, a 4% paraformaldehyde (PFA) solution was replaced and injected until muscle contraction occurred and the soles were hard. The brain was extracted by cutting the neck with scissors, peeling the scalp, cutting the muscle, peeling from the end by using forceps and scissors, long cutting the central portion of the skull, and then crushing both ear bones. The cerebrum, the cerebellum, and the myelencephalon were separated, put in PFA, reacted for 20 hours, transferred to 30% sucrose, and reacted for 3 days. The tissue was cut with a thickness of 30 μm by using a microtome in a frozen state through an OCT compound. The cut tissue piece was attached on the slide by using a brush and blocked for preventing a nonspecific antibody binding, and then reacted with a specific antibody (coupled with a fluorescence) to a protein to be reported. In the stained slide, the fluorescent degree was verified by using a confocal microscope and then the image was photographed. The photographed image was converted into numeral values by measuring the fluorescent strength for each fluorescence by analysis software.

Figure 5:
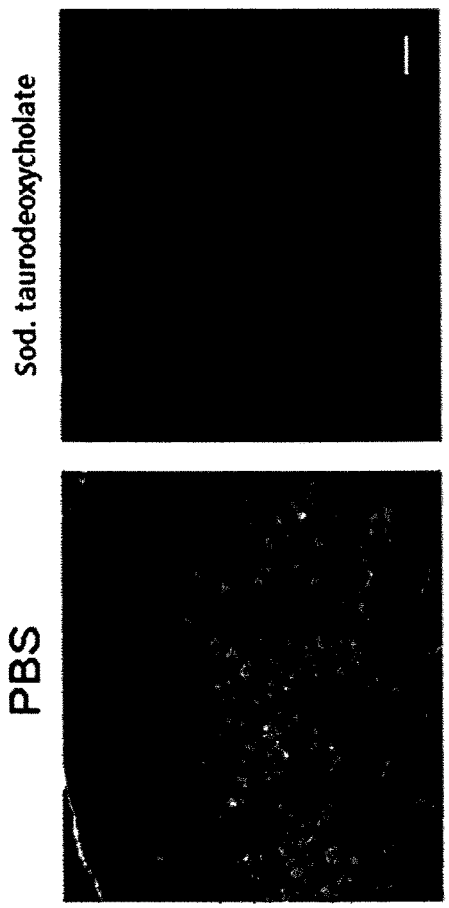
FIGS. 5 and 6 illustrate results of fluorescent-staining of an amyloid β (Aβ) plaque that causes inflammation in the frontal cortex and the hippocampus tissue in the brain of the mouse and microglia and astrocyte which are cell groups causing inflammation after 1 mg/kg of PBS or sodium taurodeoxycholate is injected to a control mouse and an Alzheimer's mouse twice per week and a total of 20 times.
Figure 5:
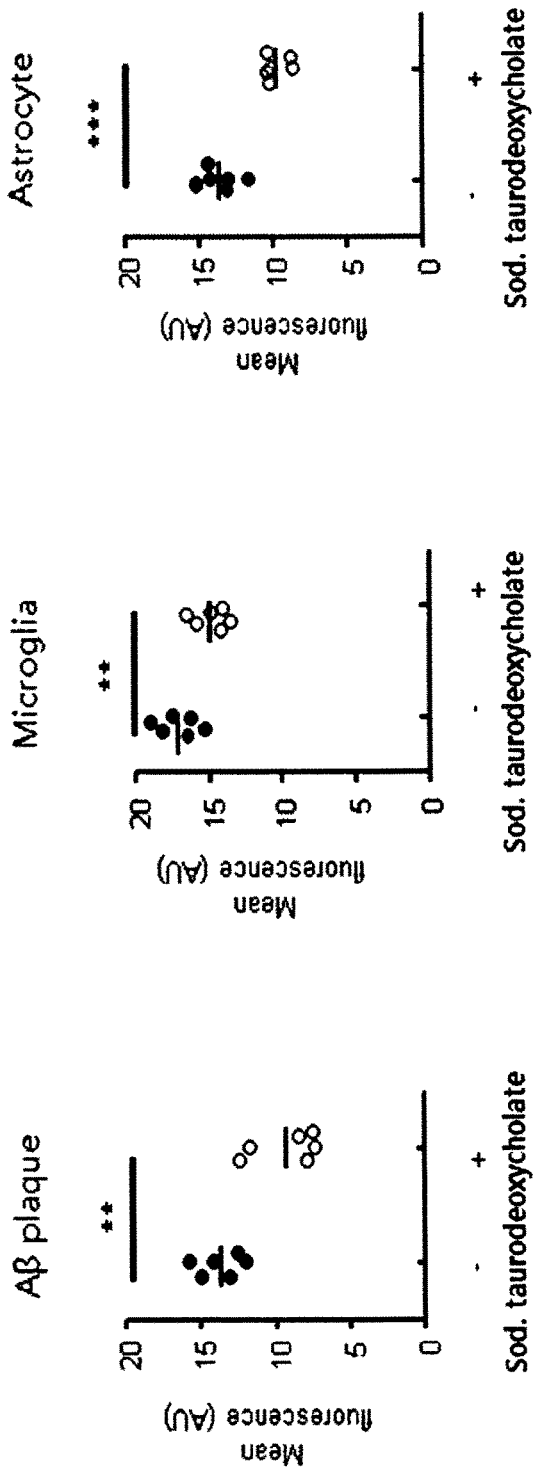
Figure 6:
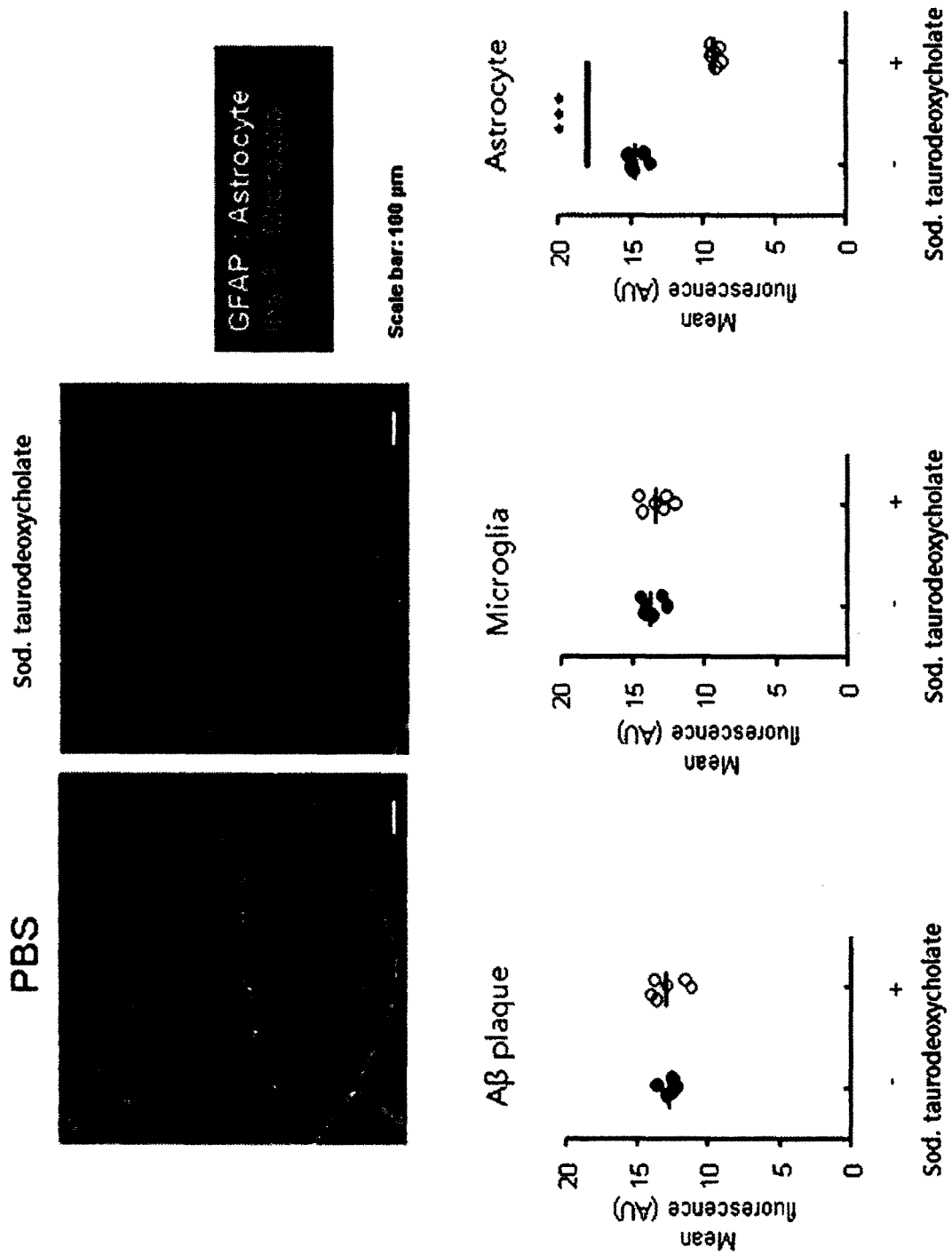

After 1 mg/kg of PBS or sodium taurodeoxycholate was injected to a control mouse and an Alzheimer's mouse (3 per group) twice a week and a total of 20 times, microglia and astrocyte which were cell groups causing the inflammatory reaction with the amyloid β plague causing the inflammatory in the frontal cortex and the hippocampus tissue in the brain of the mouse. The results were illustrated in FIGS. 5 and 6. As the experimental result, the formation of the amyloid β plague and the cell distribution of microglia and astrocyte in the frontal cortex in the brain were significantly reduced by administrating sodium taurodeoxycholate and the astrocyte cell distribution in the hippocampus area of the brain was significantly reduced.

Figure 7:
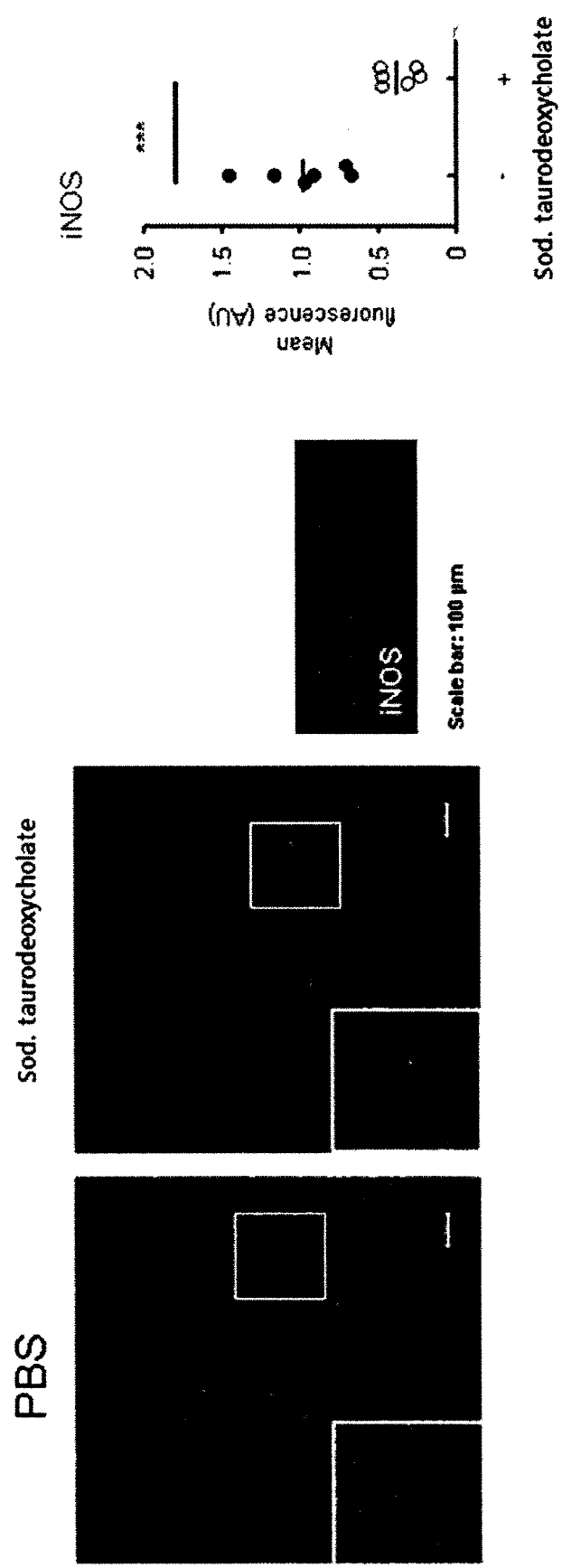
FIG. 7 illustrates a result of fluorescent-staining expression of iNOS which produces ROS exhibiting cytotoxicity in the frontal cortex in the brain of the mouse after 1 mg/kg of PBS or sodium taurodeoxycholate is injected to a control mouse and an Alzheimer's mouse twice per week and a total of 20 times.

FIG. 7 illustrates a result of fluorescent-staining expression of iNOS producing ROS exhibiting cytotoxicity in the frontal cortex area in the brain of the mouse after 1 mg/kg of PBS or sodium taurodeoxycholate was injected to the Alzheimer's mouse (3 per group) twice a week and a total of 20 times. The expression of iNOS in the frontal cortex area in the brain was significantly reduced by administrating sodium taurodeoxycholate.

Figure 8:
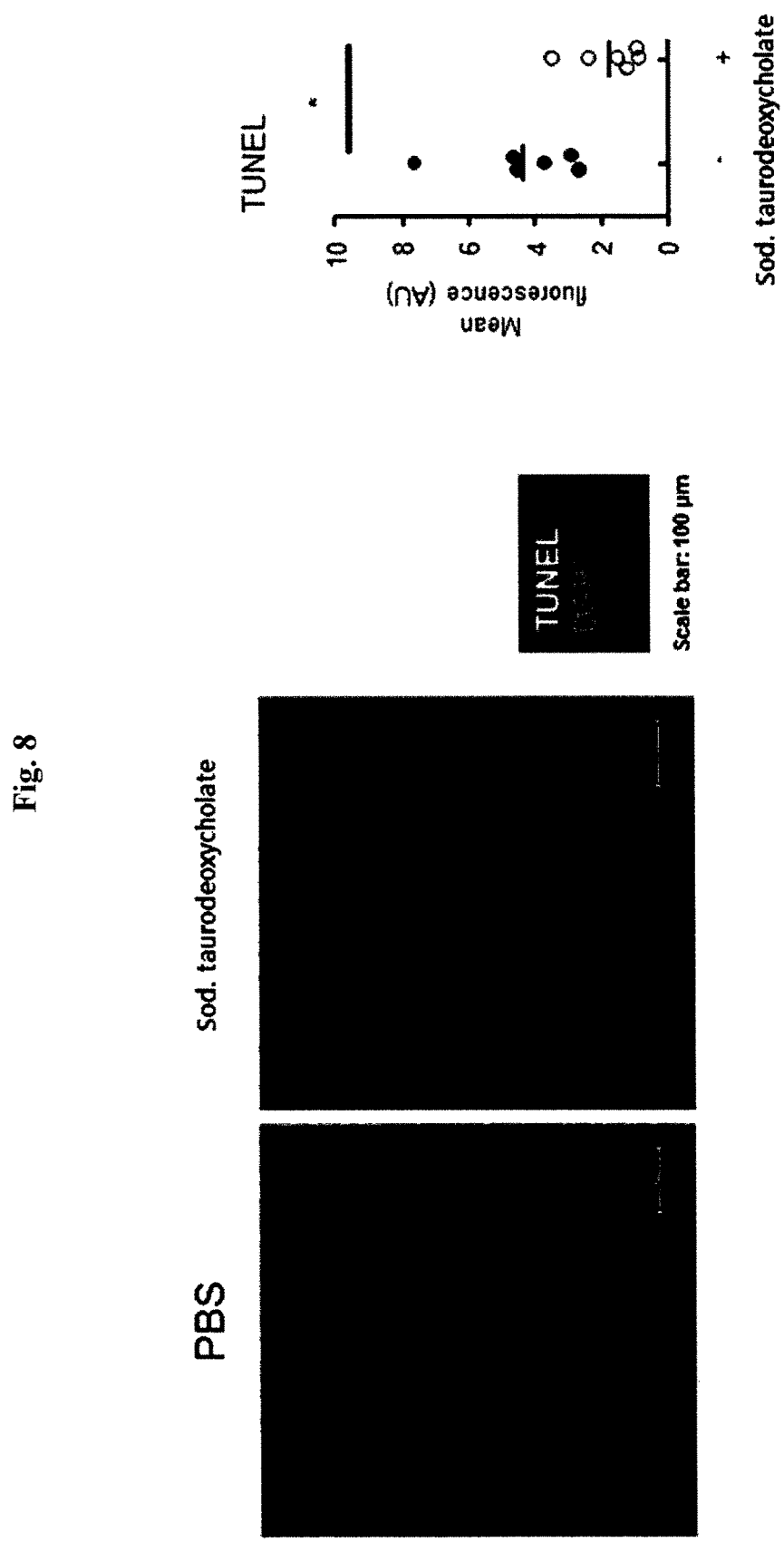
FIG. 8 illustrates a result of fluorescent-staining of an area with cytotoxicity in the frontal cortex and the hippocampus tissue by extracting the brain tissue in an Alzheimer's model mouse administrated with a drug.

The brain tissue of the Alzheimer's model mouse administrated with the drug was extracted and a reduction of the lesion such as an apoptotic lesion in the frontal cortex and the hippocampus area was measured by fluorescent-staining, and the result was illustrated in FIG. 8. The PBS or sodium taurodeoxycholate was administrated in the Alzheimer's mouse and a region damaged by apoptosis in the frontal cortex of the administrated mouse was analyzed by TUNEL staining. As the experimental result, the apoptotic region in the brain tissue was reduced by administrating sodium taurodeoxycholate.

Experimental Example 3

Analysis of Change in Blood Component by Sodium Taurodeoxycholate in Alzheimer's Animal Model

[Experimental Method: Blood analysis] The blood was obtained from the mouse by cardiac blood collection or orbital blood collection. For analyzing the inflammatory substance, the obtained blood was left for 2 hours at room temperature and centrifuged, a supernatant was taken, and each inflammatory substance was quantitatively analyzed by using a kit and equipment for bioplex. In order to analyze biochemical and hematopoietic cells, the obtained blood was put in an appropriate tube or container and applied to a biochemical analyzer and a hematology analyzer, respectively, to obtain data.

Figure 9:
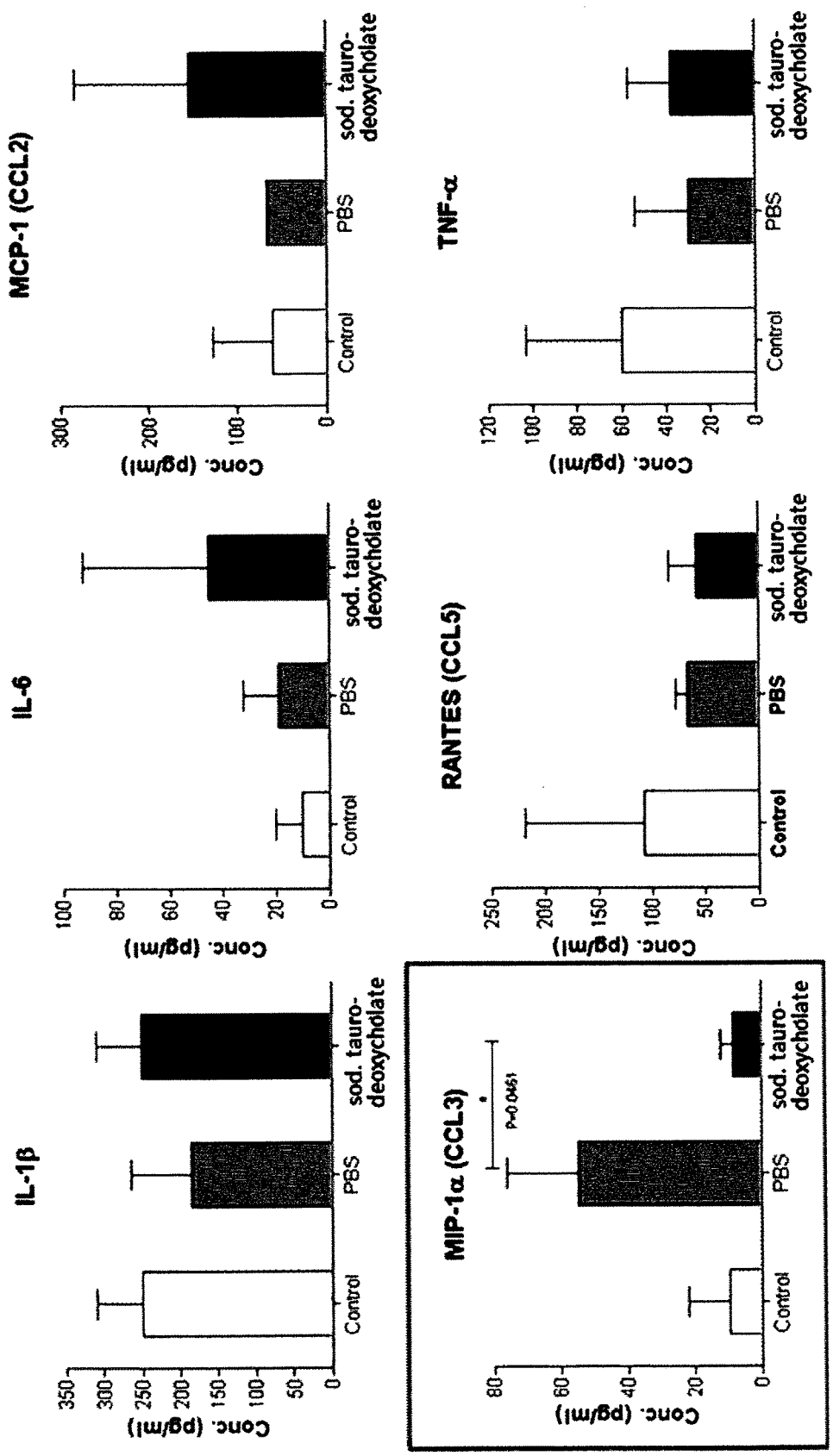
FIG. 9 illustrates a result of analyzing an inflammatory substance in the blood by extracting the blood of the mouse after 1 mg/kg of PBS or sodium taurodeoxycholate is injected to a control mouse and an Alzheimer's mouse twice per week and a total of 20 times.

FIG. 9 illustrates a result of analyzing an inflammatory substance in the blood by extracting the blood of the mouse after 1 mg/kg of PBS or sodium taurodeoxycholate is injected to a control mouse and an Alzheimer's mouse twice per week and a total of 20 times. As the result of comparing amounts of cytokines in the mouse blood for each experimental group, it was exhibited that an amount of CCL3 in the blood in the sodium taurodeoxycholate administration mouse group was increased.

Figure 10:
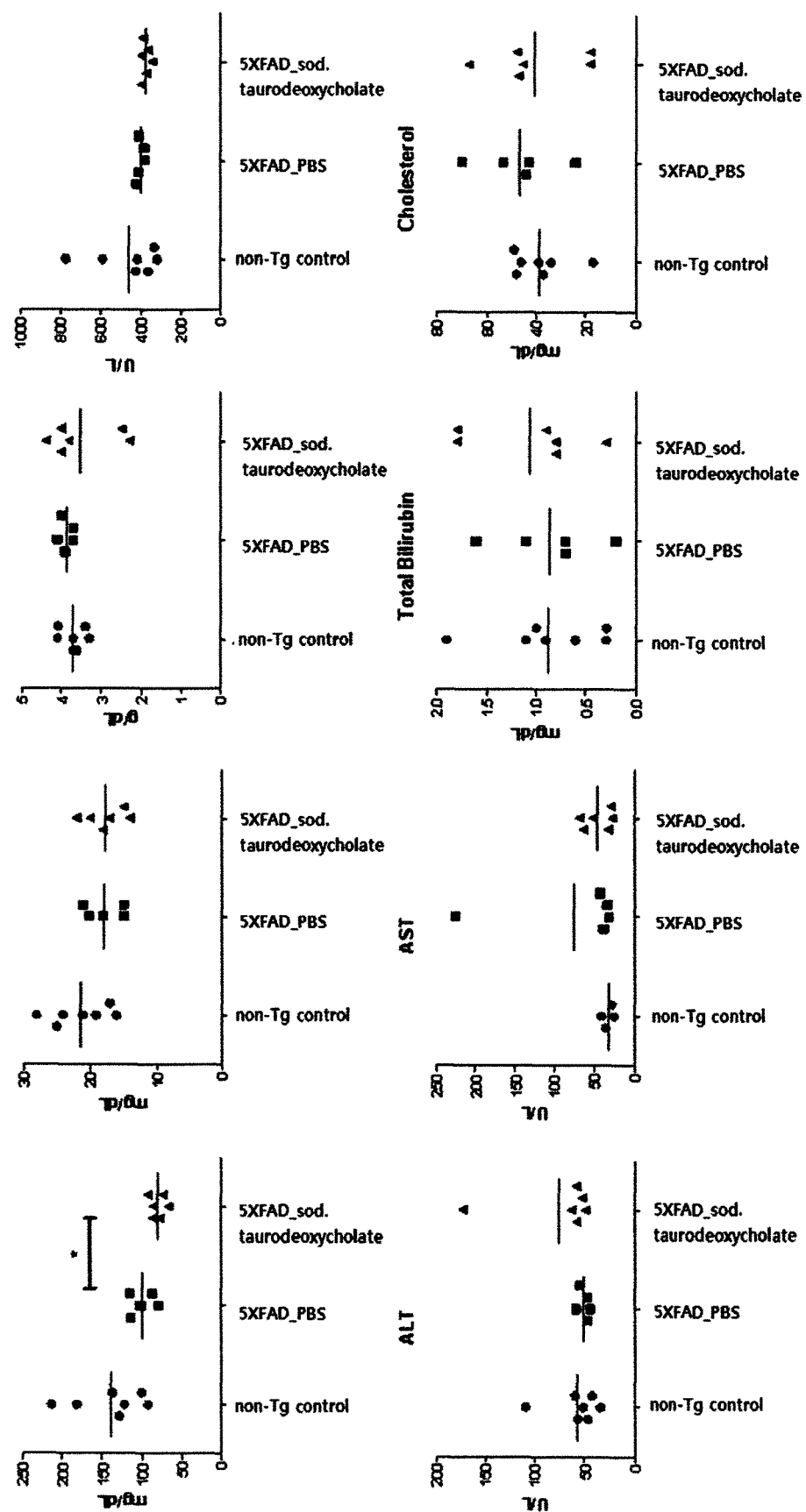
FIG. 10 illustrates a result of comparing an amount of a metabolite (glucose and the like) in the mouse blood for each experimental group after 1 mg/kg of PBS or sodium taurodeoxycholate is injected to a control mouse and an Alzheimer's mouse twice per week and a total of 20 times.

After 1 mg/kg of PBS or sodium taurodeoxycholate is injected to the control mouse and the Alzheimer's mouse twice per week and a total of 20 times, the blood of the mouse was extracted and then the biochemical components in the blood were analyzed. The result was illustrated in FIG. 10. As the result of comparing amounts of metabolites in the mouse blood for each experimental group, it was exhibited that an amount of glucose in the blood in the sodium taurodeoxycholate administration mouse group was decreased.

Hereinafter, Preparation Examples of respective formulations according to the present invention will be exemplified. The following Preparation Examples are just to help in understanding the implementation of the present invention and methods of preparing formulations according to the present invention are not limited to the following Preparation Examples.

Preparation Example 1

Preparation of Powder

Sodium taurodeoxycholate 10 mg
Sucrose 100 mg
Talc 10 mg

The ingredients were powdered and mixed and then packed in an airtight bag to prepare the powder.

Preparation Example 2

Preparation of Tablet

Sodium taurodeoxycholate 10 mg
Starch 100 mg
Sucrose 100 mg
Magnesium stearate 2 mg The ingredients were mixed and tableted according to a general tablet preparing method to prepare the tablet.

Preparation Example 3

Preparation of Capsule

Sodium taurodeoxycholate 10 mg
Crystalline cellulose 3 mg
Lactose 15 mg
Magnesium stearate 1 mg The ingredients were mixed and then filled in a gelatin capsule according to a general method of preparing the capsule to prepare the capsule.

Preparation Example 4

Preparation of Granule

Sodium taurodeoxycholate 10 mg
Soybean extract 50 mg
Glucose 200 mg
Starch 500 mg The ingredients were mixed and then added with 100 mL of 30% ethanol, dried at 60° C. to form granules and then packed in a bag to prepare the granules.

Preparation Example 5

Preparation of Pill

Sodium taurodeoxycholate 10 mg
Lactose 1,500 mg
Glycerin 1,500 mg
Starch 980 mg

The ingredients were mixed and then 4 g per 1 pill was prepared according to a general method of preparing the pills.

Preparation Example 6

Preparation of Injection

Sodium taurodeoxycholate 10 mg
Mannitol 180 mg
Sterile distilled water for injection 2,970 mg
$Na_2HPO_4 \cdot 12H_2O$ 30 mg The ingredients were mixed with the content of ingredients per 1 ampoule (2 mL) according to a general method of preparing the injection to prepare the injection.

Preparation Example 7

Preparation of Solution

Sodium taurodeoxycholate 10 mg
Isomerized glucose 10,000 mg
Mannitol 5,000 mg
Purified water suitable amount The ingredients were dissolved in purified water according to a general method of preparing the solution, added with appropriate flavor, and then filled in a bottle, sterilized to prepare the solution.

The invention claimed is:

1. A method for treating Alzheimer's-related disease or dementia-related disease selected from the group consisting of cerebral amyloid angiopathy, cognitive impairment, mild cognitive impairment, Alzheimer's disease-related attention deficit symptoms, Alzheimer's disease-related neural degeneration, degenerative dementia, senile dementia, cerebral vascular dementia, alcoholic dementia, parkinson's disease-related dementia, tic disorder, and corticobasal ganglionic degeneration, the method comprising administering a pharmaceutical composition containing a pharmaceutically effective amount of G protein-coupled receptor19 (GPCR19) agonist or a pharmaceutically acceptable salt thereof as an active ingredient to an individual having the disease, wherein the GPCR19 agonist is sodium taurodeoxycholate.

2. The method for treating Alzheimer's-related disease or dementia-related disease according to claim 1, wherein the pharmaceutical composition is formulated in the form of oral, rectal, intravenous, intramuscular, intraperitoneal, subcutaneous, intranasal, or percutaneous formulation.

3. The method for treating Alzheimer's-related disease or dementia-related disease according to claim 1, wherein the GPCR19 agonist or its pharmaceutically acceptable salt is administered with a dose of 0.1 mg/kg/day to 1000 mg/kg/day.

4. The method for treating Alzheimer's-related disease or dementia-related disease according to claim 1, wherein the GPCR19 agonist or its pharmaceutically acceptable salt is administered with a dose of 1 mg/kg/day to 500 mg/kg/day.

5. The method for treating Alzheimer's-related disease or dementia-related disease according to claim 1, wherein the GPCR19 agonist or its pharmaceutically acceptable salt is administered with a dose of 10 mg/kg/day to 100 mg/kg/day.

6. The method for treating Alzheimer's disease or dementia according to claim 1, wherein the GPCR19 agonist or its pharmaceutically acceptable salt is administered 1 to 3 times per week.

* * * * *